United States Patent
Amling et al.

(10) Patent No.: US 7,316,646 B2
(45) Date of Patent: Jan. 8, 2008

(54) UNIFIED ELECTRICAL AND ILLUMINATION CABLE FOR ENDOSCOPIC VIDEO IMAGING SYSTEM

(75) Inventors: Marc R. Amling, Santa Barbara, CA (US); David Chatenever, Santa Barbara, CA (US); Bruce L. Kennedy, Santa Barbara, CA (US); Barry A. Mirrer, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 0 days.

(21) Appl. No.: 10/720,571

(22) Filed: Nov. 24, 2003

(65) Prior Publication Data

US 2004/0106851 A1 Jun. 3, 2004

Related U.S. Application Data

(62) Division of application No. 10/249,278, filed on Mar. 27, 2003, and a division of application No. 10/034,271, filed on Dec. 28, 2001, now Pat. No. 6,960,161.

(51) Int. Cl.
*A61B 1/04* (2006.01)
*A61B 1/07* (2006.01)

(52) U.S. Cl. ............... 600/109; 600/110; 600/132; 600/178; 600/182; 348/73

(58) Field of Classification Search ............... 600/110, 600/109, 112, 132, 178, 182; 348/68, 73, 348/75; 385/101
See application file for complete search history.

(56) References Cited

U.S. PATENT DOCUMENTS

| | | | | |
|---|---|---|---|---|
| 4,356,534 A | * | 10/1982 | Hattori | ............... 362/574 |
| 4,402,313 A | | 9/1983 | Yabe | |
| 4,667,230 A | * | 5/1987 | Arakawa et al. | ............... 348/76 |
| 4,963,960 A | | 10/1990 | Takami | |
| 5,007,408 A | | 4/1991 | Ieoka | |
| 5,010,876 A | | 4/1991 | Henley et al. | |
| 5,239,983 A | | 8/1993 | Katsurada | |
| 5,242,315 A | | 9/1993 | O'Dea | |
| 5,311,859 A | * | 5/1994 | Monroe et al. | ............. 600/112 |
| 5,419,717 A | | 5/1995 | Abendschein et al. | |

(Continued)

FOREIGN PATENT DOCUMENTS

DE    38 08 011    9/1988

OTHER PUBLICATIONS

Interface Circuits for TIA/EIA-644 (LVDS) Design Notes, Copyright 1998, Texas Instruments Incorporated.

*Primary Examiner*—John P. Leubecker
(74) *Attorney, Agent, or Firm*—St. Onge Steward Johnston & Reens LLP

(57) ABSTRACT

A video imaging system including an endoscopic device, a camera, a camera control unit and a light source, the camera coupled to the camera control unit and light source via a single cable connection. The cable is advantageously provided as a pair of wires and a light guide where image data and camera information is transmitted over the pair of wires from the camera to the camera control unit, the data and information being multiplexed on the pair of wires; and command signals are sent from the camera control unit to the camera, the command signals based on the received camera information for control of the camera.

14 Claims, 7 Drawing Sheets

U.S. PATENT DOCUMENTS

| | | | |
|---|---|---|---|
| 5,509,096 A * | 4/1996 | Easley | 385/89 |
| 5,569,158 A * | 10/1996 | Suzuki et al. | 600/110 |
| 5,575,757 A | 11/1996 | Kennedy et al. | |
| 5,702,345 A * | 12/1997 | Wood et al. | 600/109 |
| 5,716,323 A * | 2/1998 | Lee | 600/134 |
| 5,852,697 A | 12/1998 | Williams et al. | |
| 5,896,166 A | 4/1999 | D'Alfonso et al. | |
| 5,974,464 A * | 10/1999 | Shin et al. | 709/231 |
| 5,976,070 A * | 11/1999 | Ono et al. | 600/110 |
| 6,261,226 B1 * | 7/2001 | McKenna et al. | 600/109 |
| 6,293,910 B1 * | 9/2001 | Yamakita et al. | 600/132 |
| 6,313,868 B1 | 11/2001 | D'Alfonso et al. | |
| 6,388,702 B1 * | 5/2002 | Konomura et al. | 348/74 |
| 6,503,195 B1 * | 1/2003 | Keller et al. | 600/160 |
| 6,638,212 B1 * | 10/2003 | Oshima | 600/109 |

* cited by examiner

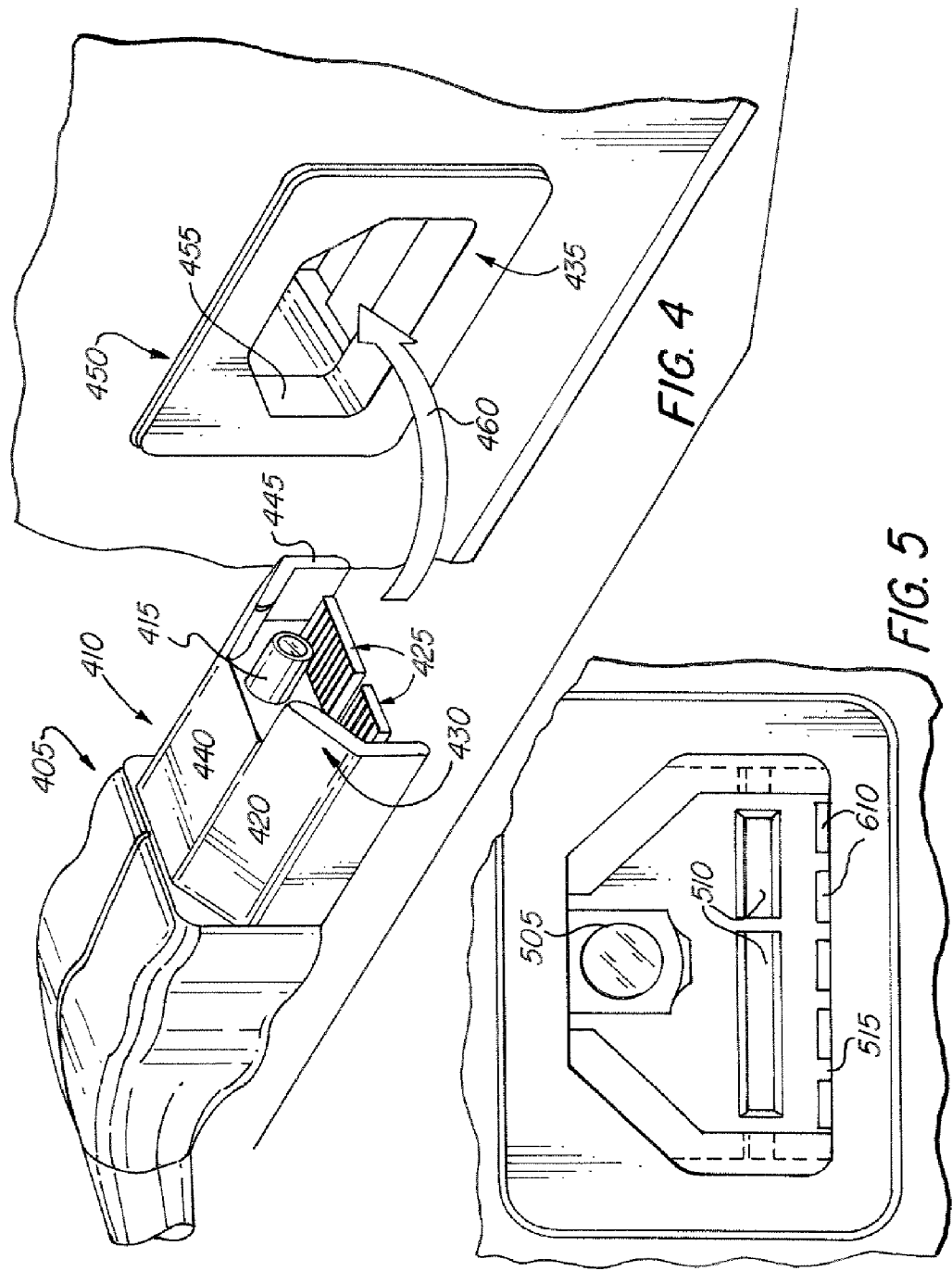

UNIFIED ELECTRICAL AND ILLUMINATION CABLE FOR ENDOSCOPIC VIDEO IMAGING SYSTEM

PRIOR APPLICATION

This application is a divisional of U.S. patent application No. 10/034,271, filed on Dec. 28, 2001, now U.S. Pat. No. 6,960,161, issued Nov. 1, 2005, and is a divisional of copending U.S. patent application No. 10/249,278, filed Mar. 27, 2003.

FIELD OF THE INVENTION

This application relates to an endoscopic video imaging system for transmitting communication signals and illuminating light along a single cable between a camera control unit and a camera head.

BACKGROUND OF THE INVENTION

The field of video endoscopy, to which the present invention generally relates, includes medical diagnostic and therapeutic disciplines that utilize endoscopes to penetrate and view otherwise inaccessible body cavities utilizing minimally invasive surgical procedures. Coupling of video imaging cameras (incorporating solid-state imagers) to endoscopes, for image reproduction, has become standard within the field. Endoscopic video cameras (hereinafter referred to as "camera heads"), are most advantageously small and lightweight for ease of use by medical personnel, and typically incorporate either single or multiple solid-state imagers. Some special purpose endoscopes have integrated (built-in) solid-state imagers, which do not facilitate direct viewing of internal body cavities by medical personnel without an accompanying video imaging system and display. To achieve the desired size and weight, camera head and/or integrated endoscope-camera assembly electronics are typically separated physically from the majority of circuitry required to process and output high-quality, color video images.

In known video imaging systems, interconnection between camera control units ("CCUs") and camera heads is achieved by means of a cable, with usually one cable end permanently fixed to the camera head, while the other cable end is detachably connected to the CCU using a connector. Similar to the camera head itself, it is advantageous that cables be small in diameter and lightweight, but rugged enough to withstand repeated sterilization, accidental gurney wheel "run-over," and the like.

Most cables for endoscopic video cameras include a fiber optic light guide for illumination, the fiber optic light guide being separately distinct from the cable transmitting electronic video signals. Because the operating room has limited space, extra medical equipment typically creates a substantial inconvenience for medical personnel.

Existing interconnections between camera heads and CCUs typically comprise dedicated parallel wires to provide greater data carrying capacity. It is meant by "dedicated parallel wires" that each specific signal is transmitted by means of an individual wire, either single for power and control signals or shielded coax for image data, between a camera head and CCU. However, a disadvantage of providing dedicated parallel wires is that typically twenty to thirty separate lines are required to control, energize and receive image data from camera heads, with most signal lines requiring a dedicated connector pin. The more channels required, the greater the diameter, size and corresponding weight of the cable bundle. The larger this bundle becomes, the more likely it is to interfere with medical personnel's use of the video imaging system. Moreover, utilizing dedicated parallel wire type cabling is undesired when additional functionality is required and added to either the camera head or CCU. To accommodate this new functionality, additional wiring must be incorporated in the cable bundle, requiring equipment redesign and subsequent purchase by customers. Also, as video imaging systems develop, CCUs are becoming programmable for compatibility with various types of camera heads, are adding new control features and are processing different types of video signals.

Typically a combined optical electrical connector is provided with optical and electrical components that can move relative to one another within the body of the connector. Disadvantageously, correct and precise adjustments of the respective components are difficult and time consuming, where the poor connection often results in poor system performance. In addition, the separate cables for transmitting illuminating light and information may become tangled thereby becoming an inconvenience for the user.

It is therefore desired to provide a video imaging system that utilizes relatively few channels in order to reduce the size and corresponding weight of the cable, while still maintaining high video image quality.

It is also desired to provide a video imaging system that incorporates the light source guide for illumination into a single cable with the channel transmitting information between the camera head and camera control unit.

It is further desired to provide a video imaging system that has a rugged cable assembly that will not be damaged by day-to-day use in the operating room.

It is still further desired to provide a connector where electrical and optical components are in a fixed spatial relationship to one another and are integrated into a single connector so as not to tangle with one another.

SUMMARY OF THE INVENTION

These and other objects of the invention are achieved in one advantageous embodiment by providing a video imaging system, comprising a camera head for generating image data, a camera control unit, and a cable for connecting the camera head to the camera control unit. The cable includes in a single protective jacket enclosing, at least one channel for transmitting information between the camera head and the camera control unit, and a light source guide for transmitting light to the camera head for use in generating the image data.

In another advantageous embodiment a video imaging system is provided comprising a camera head for generating image data, and a cable for transmitting the image data, the cable including in a single protective jacket enclosing, at least one electrical channel for transmitting the image data from the camera head to a camera control unit, and a light source guide for transmitting light to the camera head for use in generating the image data.

In a further advantageous embodiment a video imaging system is provided comprising a camera head for generating image data, a camera control unit and a cable, for connecting the camera head to the camera control unit, the cable including, in a single protective jacket enclosing, at least one electrical channel for transmitting information between the camera head and the camera control unit, and a light source guide for transmitting light to the camera head for use in generating the image data.

In yet another advantageous embodiment a video imaging system is provided comprising a receptacle having optical and electrical components, for receiving a connector and a connector detachably connectable with the receptacle. The receptacle includes a body with a front surface, a light source guide and an electrical edge-connector terminating beyond the front surface, the light source guide and electrical edge-connector engaging the optical and electrical components, respectively, upon advancement of the connector into the receptacle.

A video imaging system is also provided comprising a camera for generating image data, a control unit for controlling the camera and a channel for transmitting a control signal in the nature of camera operating information and the image data from the camera to the control unit. The control signal and the image data are multiplexed on the channel and a light guide transmits light to an object, wherein the camera is receptive of light reflected off of the object thereby generating the image data.

The electrical and optical components are in a fixed spatial relationship within the receptacle, so that these components are aligned with electrical and optical connectors of the plug, respectively, when the plug is advanced into the receptacle.

The invention and its particular features and advantages will become more apparent from the following detailed description considered with reference to the accompanying drawings.

BRIEF DESCRIPTION OF THE DRAWINGS

FIG. 4 is a depiction of the connector assembly to be advanced into the receptacle.

FIG. 5 is a front section view of the receptacle.

DETAILED DESCRIPTION

Figure 1:
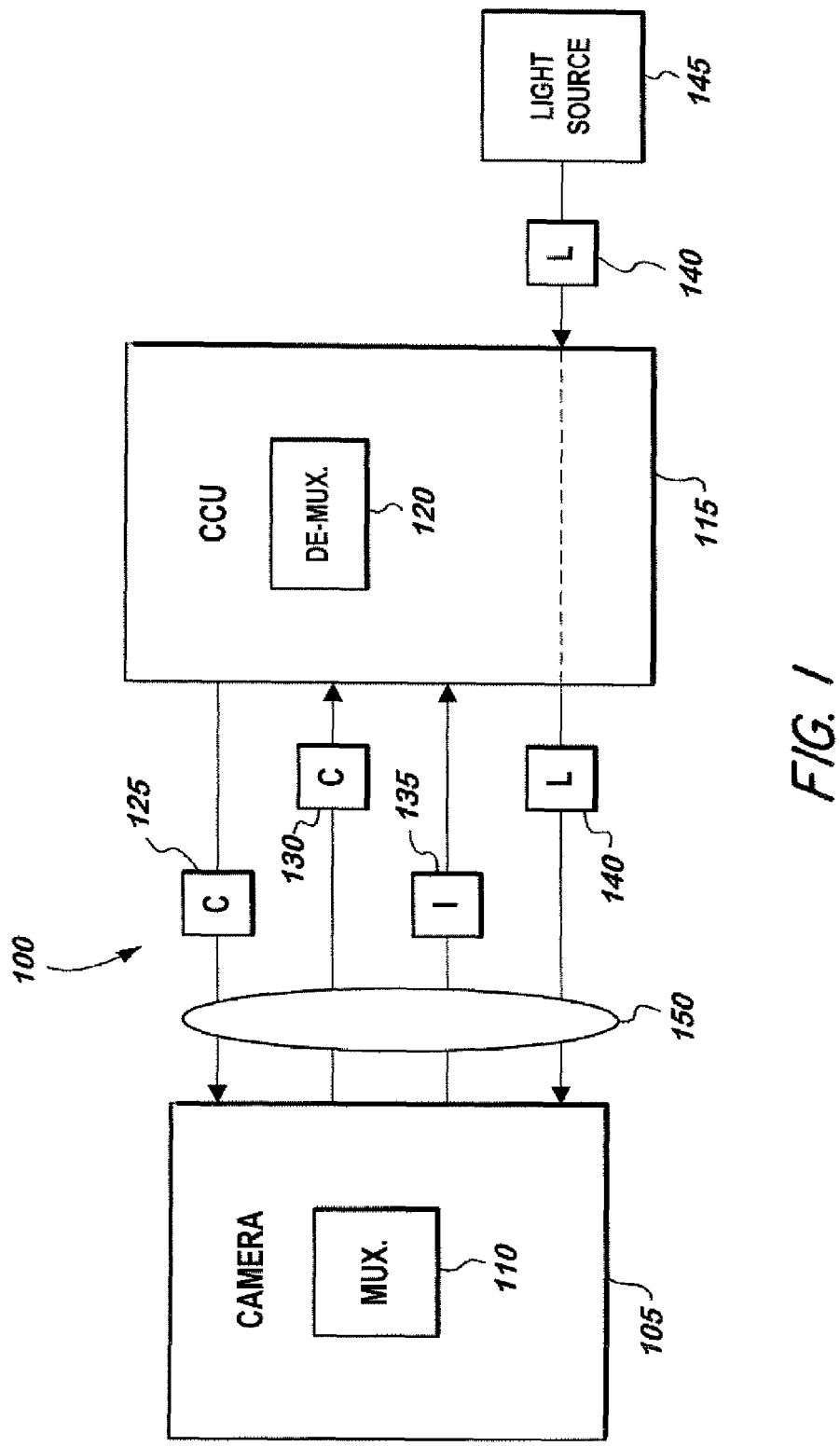
FIG. 1 is a block diagram of the video imaging system illustrating the camera head, the channel connections, the camera control unit, and the illumination light source.

FIG. 1 illustrates an advantageous embodiment of the video imaging system 100. A camera head 105 is provided having a multiplexer 110 for multiplexing image data and control signals. A camera control unit 115 is provided with a multiplexer 120 for receiving and processing the multiplexed signal from the camera head 105. A command signal channel 125 is provided interconnecting camera head 105 and camera control unit 115. The command signal channel 125 allows command signals to be sent from the camera control unit 115 to the camera head 105. Command signals include any signal transmitted from the camera control unit to the camera head. A control signal channel 130 is provided interconnecting camera head 105 and camera control unit 115. The control signal channel 130 allows control signals to be sent from the camera head 105 to the camera control unit 115. Control signals include any signal transmitted from the camera head except image data, and may include signals such as: software programs, operating information, timing signal data, camera head identification information, camera use information and the like. An image data channel 135 is provided interconnecting camera head 105 and camera control unit 115. The image data channel 135 allows image data to be sent from the camera head 105 to the camera control unit 115 for processing.

Through multiplexer 110 the control signal 130 and the image data 135 are transmitted down the same physical pair of wires, and the command signal 125 is transmitted on a second pair of wires.

Alternatively, for further cable size reduction, the command signal may also be multiplexed with the control signal and image data and therefore be transmitted down the same physical wire, thereby reducing the number of wires to one pair. It is well known in the art that multiplexers 110 and 120 may perform both multiplexing and de-multiplexing functions. The video imaging system utilizes a digital serial protocol such as Low-Voltage Differential Signaling.

Further, it will be apparent to those skilled in the art that additional pairs of wires may be supplied for image data, control signals, and command signals for future data carrying requirements as new systems become available.

A light source guide 140 is also furnished to provide illuminating light from light source 145, through camera control unit 115, to camera head 105.

A single protective jacket 150 is also provided, for enclosing the command signal channel 125, the control signal channel 130, the image data channel 135, the light source guide 140, and any additional channels that may be utilized.

Figure 2:
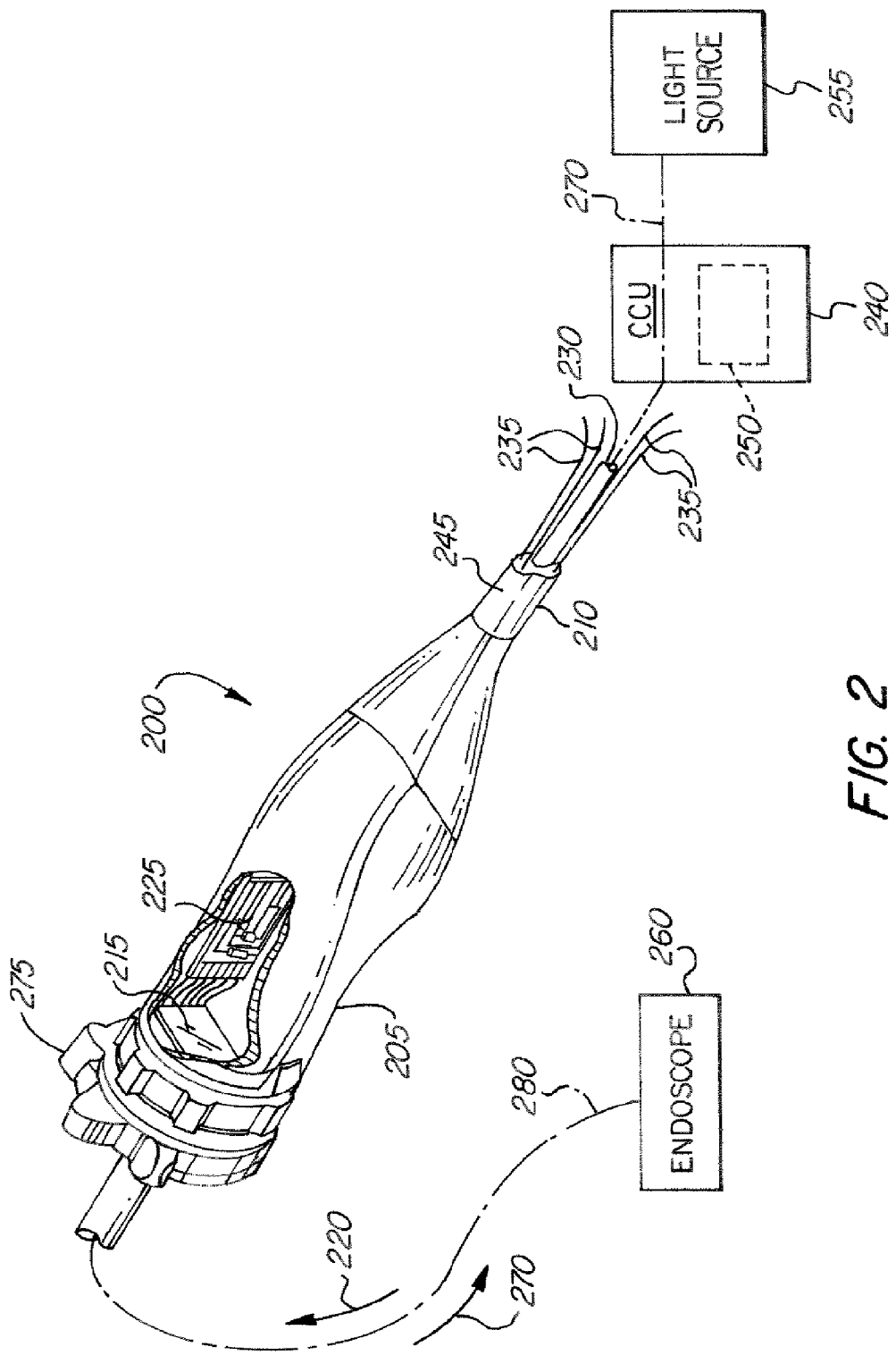
FIG. 2 is a depiction of a camera head with a sectional view of the attached cable assembly, the camera control unit and the light source.

FIG. 2 illustrates an advantageous embodiment of the video imaging system 200. A camera head 205 is provided having a cable 210. In this embodiment, the cable 210 is permanently attached to the camera head 205. However, it is contemplated that the cable 210 may also be detachably connected to the camera head 205. The camera head 205 is equipped with an imager 215 for receiving photonic energy 220 reflected off an object (not shown). The camera head 205 is also equipped with a multiplexer 225 for multiplexing various signals generated by the camera head 205. The various signals may include for instance: image data generated by the imager 215, and control signals generated by the camera head 205. In FIG. 2, the video imaging system 200 further comprises an endoscope 260 wherein the camera head 205 receives light 270 from the light source 255 and transmits the light 270 to the endoscope 260. The light 270 is transmitted through the camera head 205. The light 270 is transmitted from the camera head 205 to the endoscope 260 through an intermediate coupling 275 mounted to the camera head 205 and a cable 280 for connecting the intermediate coupling 275 and the endoscope 260.

Figure 9:
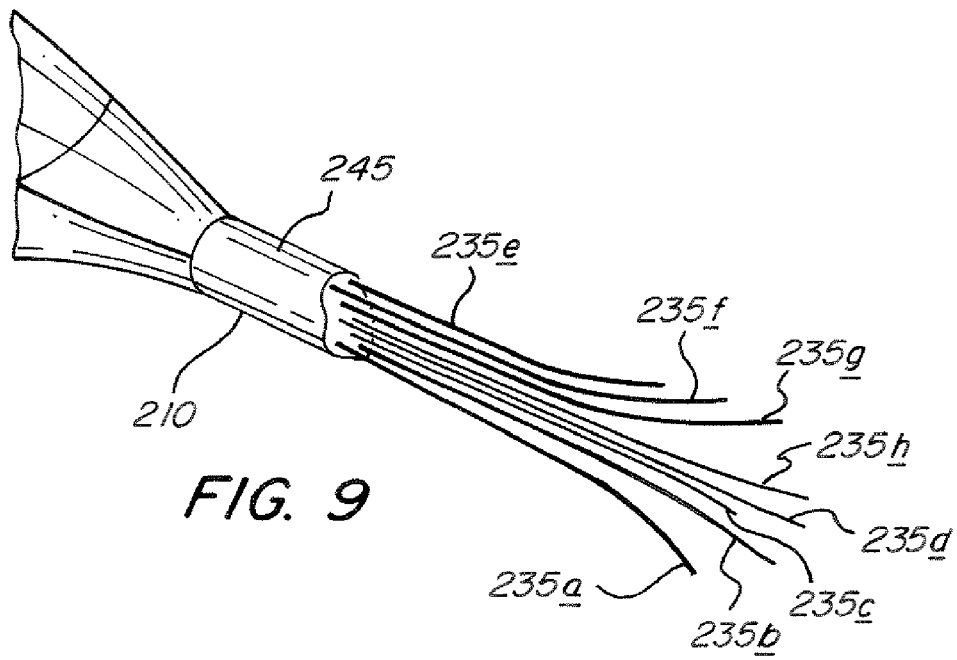
FIG. 9 is a depiction of a section of the camera head of FIG. 2 showing four channels comprising eight electrical conductors.
Figure 10:
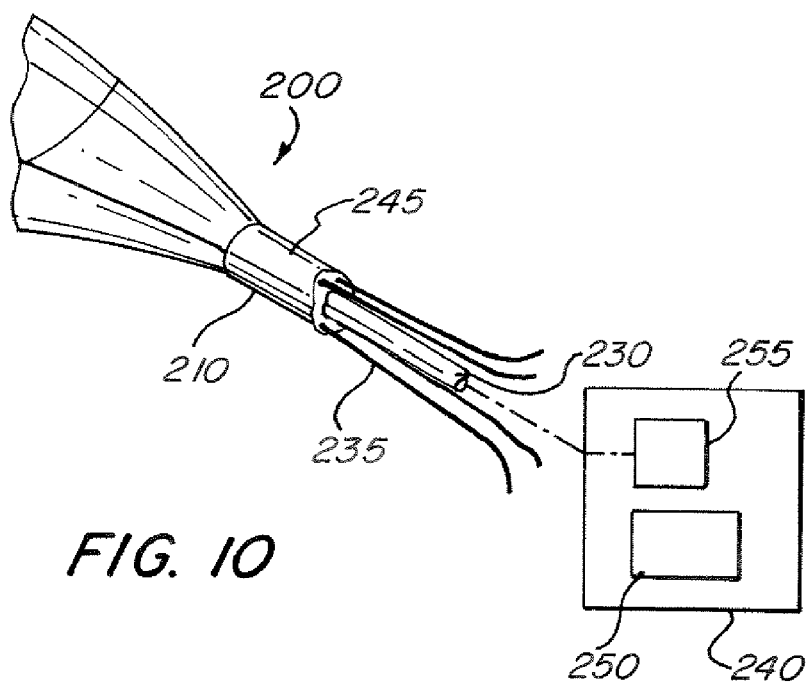
FIG. 10 is a depiction of a light source mounted within a camera control unit.

The cable 210 includes a light guide channel 230 for transmitting illuminating light to the camera head 205. The cable 210 further includes data channels 235 for transmitting data to and from the camera head 205 and the CCU 240. Four data channels 235 are depicted in FIGS. 2 and 10, however it will be obvious to one skilled in the art that fewer or more data channels 235 may be utilized. Image data and control signals are multiplexed in the camera head 205 by the multiplexer 225 for transmission along data channels 235. One of the data channels 235 may be utilized for the multiplexed signal, or any number or combination of data channels 235 may be utilized. The cable 210 is also provided with a protective jacket 245, encasing the light guide channel 230 and the data channels 235. FIG. 9 depicts a section of the camera head of FIG. 2 showing four channels comprising eight electrical conductors 235*a-h*.

In this advantageous embodiment it is contemplated that the CCU 240 may also be provided with a multiplexer 250 for multiplexing command signals, and for demultiplexing the image data and control signals sent from the camera head 205. It is contemplated that multiplexers 225 and 250 may both provide both multiplexing the demultiplexing functions. A light source 255 is also provided for generating illuminating light for the transmission by the light guide channel 230 to the camera head 205. The cable 210 is detachably connected to the CCU 240 as disclosed in FIGS. 3-8.

Figure 3:
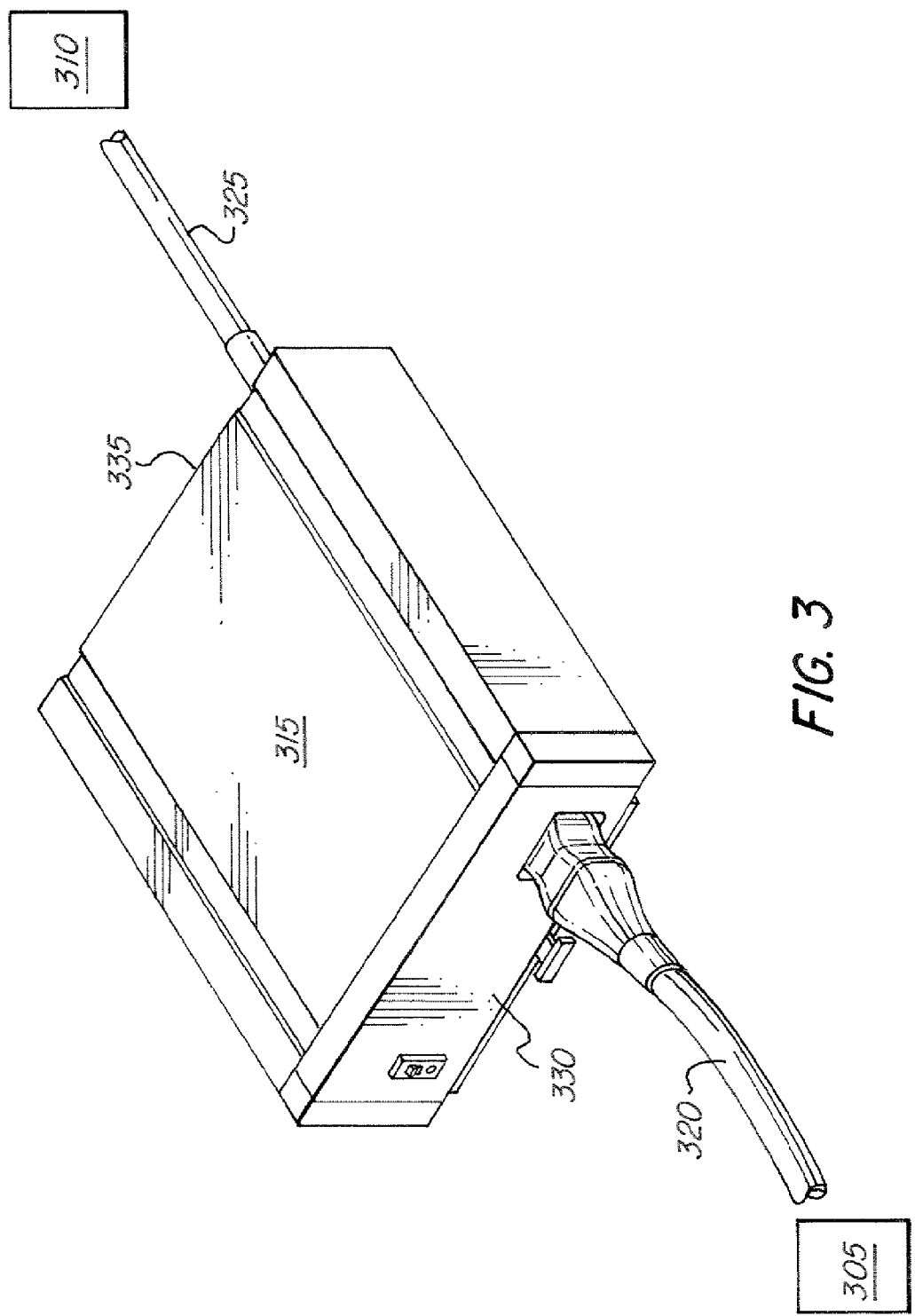
FIG. 3 is a depiction of the camera control unit, the receptacle, the connector attached to the cable, and the light source.

Referring to FIGS. 3-8, and particularly FIG. 3, a connector assembly for an endoscope assembly provides a connection between a camera head 305 and a source of light 310 through a CCU 315 having a front portion 330 and a rear portion 335. A cable 320 extending from the camera head carries a light source guide and at least one wire pair transmitting electronic signals between the CCU and the camera head. A light source cable 325 extends from the light source 310 through the CCU and directly engages the cable 320 in the CCU.

Referring to FIG. 4, the connector assembly includes a plug 405 provided with a molded body 410. A light connector 415 extends from a front surface 420 of the molded body 410, whereas an electrical connection, which is mostly encased in the molded body 410, has a keyed edge connector 425 projecting beyond the front surface 420. As clearly seen in FIG. 4, the light connector 415 and the keyed edge connector 425 extending through the plug 405 are in a fixed spatial relationship.

The keyed edge connector 425 can be selected from a great variety of electrical connectors and, in the present case, is shown as a printed wiring board. The keyed edge connector 425 preferably terminates in the same plane as the light connector 415. However, it is contemplated within the scope of the invention to provide an arrangement where the keyed edge connector 425 and the light connector 415 extend from the front surface 420 of the molded body 410 at different distances. Such structure provides for mating components of the receptacle to be similarly positioned with respect to one another. The light connector 415 is shown above the keyed edge connector 425. However, it is possible to arrange the components in many different arrangements. It is however, advantageous to maintain a fixed spatial relationship as to the components in utilizing the various arrangements.

As further shown in FIG. 4, the molded body 410 has keying surfaces 430 for the plug as well as protection for the light connector 415 and the keyed edge connector 425 by extending from the front surface 420 beyond these connectors. The plug 405 is introduced through the front side 330 of the CCU (FIG. 3) into a receptacle opening 435. Each of the keying surfaces 430 has the geometry that allows the plug to enter the receptacle only in a predetermined spatial position. Exclusively, for illustrative purposes, each of the keying surfaces 430 of FIG. 4 has two straight portions 440, 445 inclined with respect to one another.

The keying surfaces 430 are shaped and sized to place the plug 405 in a unique spatial position with respect to a receptacle 450 by extending complementary to an inner peripheral surface 455 of the opening 435 at the entry point for the plug 405. The plug is advanced 460 into the receptacle 450 as indicated to provide engagement between light connector 415 and keyed edge connector 425 with optical component 505 and electrical component 510 respectively, as shown in FIG. 5. The position of the optical component 505 and electrical component 510 is a mirror image of the configuration of the light connector 415 keyed edge connector 425 respectively. Furthermore, a grounding plate 605, seen in FIG. 6, is provided with a plurality of spaced-apart, resilient fingers 610 seen in FIGS. 5 and 6, which extend slightly above a bottom edge 515 of the opening 435 seen in FIG. 4.

Figure 6:
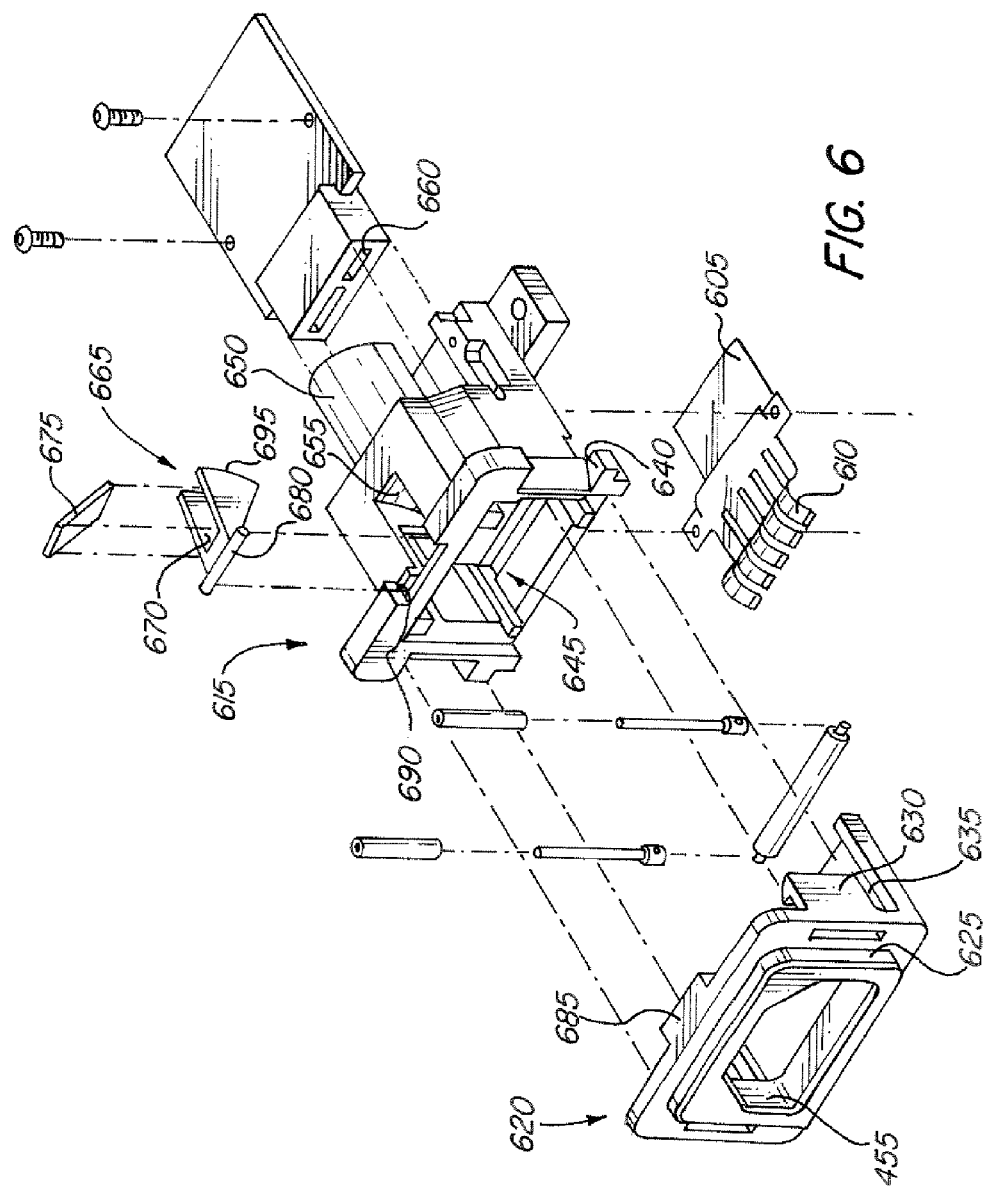
FIG. 6 is an assembly drawing of the receptacle.

The receptacle 450 has a housing 615, as seen in FIG. 6, provided with a detachable front panel 620. The front panel 620 has a front flange 625 lying flush with the front side 330 of the CCU when assembled. To provide a correct position of the front panel 620 with respect to the housing 615, each of the sides 630 has an elongated recess 635 receiving a respective lug 640 formed on the housing 615.

The housing 615 receives an optical connector component of the light source cable 325 extending through the rear portion 335 of the CCU and the light connector 415 and the keyed edge connector 425 of the plug 405. A chamber 645 is sized so that the molded body 410 of the plug 405 extends at its full length into the receptacle 450 in an engaged position where the light connector 415 and the keyed edge connector 425 of the plug 405 engage respective components of the receptacle 450.

Figure 7:
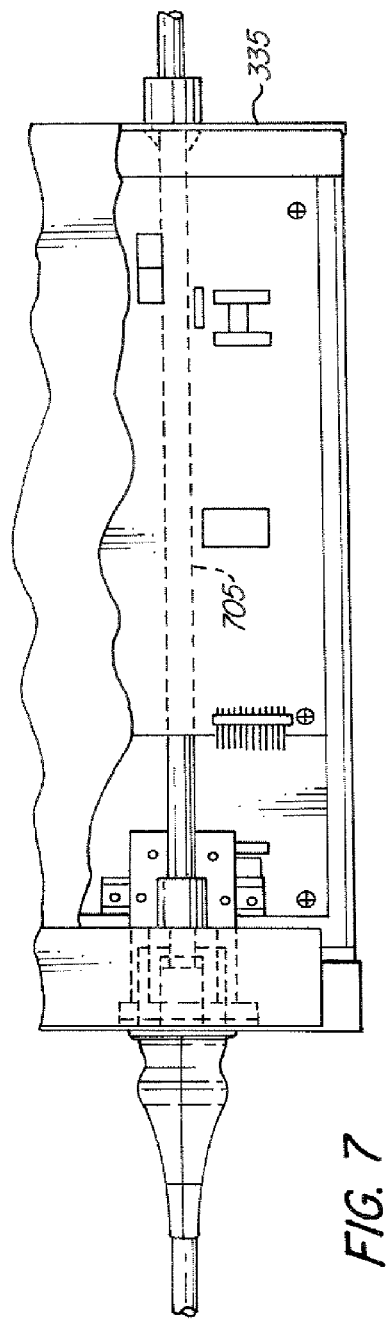
FIG. 7 is a top section view of the camera control unit of FIG. 1 depicting the light source guide entering the camera control unit from the rear and connecting with the cable through the receptacle.
Figure 8:
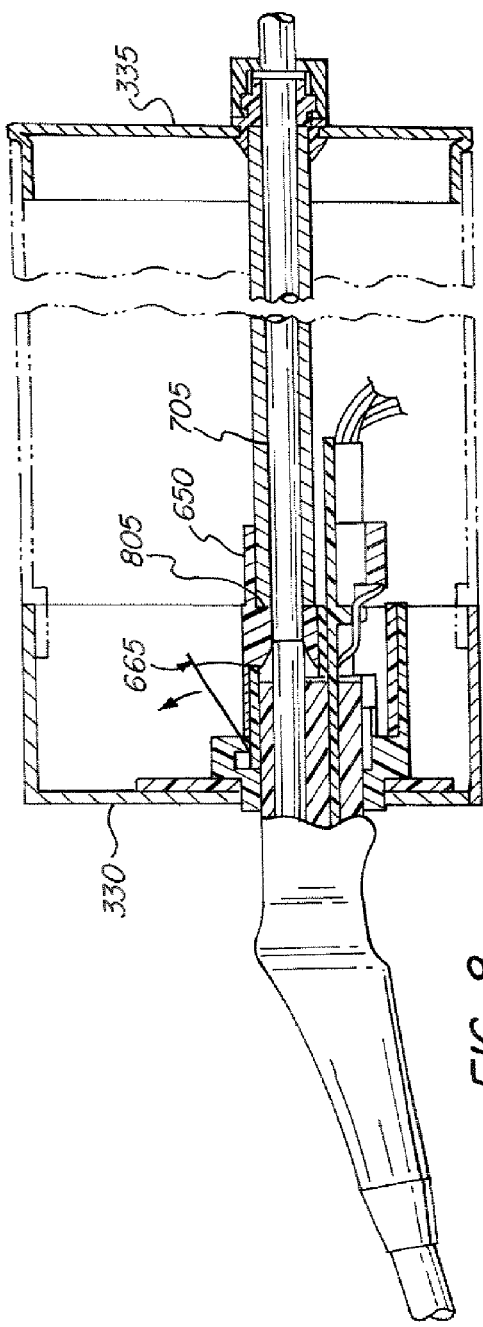
FIG. 8 is a side section view of the camera control unit of FIG. 1 depicting the light source guide entering the camera control unit from the rear and connecting with the cable through the receptacle.

The housing 615 is further provided with a collar 650 extending toward the rear portion 335 of the CCU 315 and receiving a guide element 705 as seen in FIG. 7, that linearly spans the distance between the rear portion 335 of the CCU 315 and the receptacle 450. An inner end of the guide element 705 slides against the collar 650 and abuts a seat 805 as seen in FIG. 8, of the housing 615 of the receptacle 450. An end of the light source cable 325 having an optical connection component extends beyond the guide element 705 and terminates in a rear wall 655 of the chamber 645. Thus, the light source cable 325 is mounted within the receptacle 450 in a fixed spatial position and is aligned with the cable 320 after the molded body 410 of the plug 405 is registered with the opening 435 of the front panel 620.

To provide an electrical connection between the camera head and the remaining CCU components, the receptacle 450 includes an electrical component 510 comprising a socket 660. The socket 660 is in the same fixed spatial relationship with the optical component 505.

To prevent the high intensity light from the source of light 310 from escaping the CCU 315, the receptacle 450 is provided with a light deflector 665, which is mounted to block the light from exiting the CCU 315 from the light source cable 325 when the plug 405 is withdrawn from the receptacle 450. A bottom portion 675 bridges spaced apart walls 670 of the light deflector 665. The deflector 665 is sized so that the keying surfaces 430 of the plug 405 contacts the bottom portion 675 as the plug 405 is advanced into the receptacle 450. The light deflector 665, which is pivotally mounted by means of a pin 680 extending between the spaced apart walls 670 and mounted on the housing 615 of the receptacle 450, swings out of a light path. As the plug is withdrawn from the receptacle 450, the light deflector 665 swings back into the light path to confine the light inside the CCU 315.

To ensure that the pin 680 is not displaced from the housing 615, a flange 685 provided on the front panel 620 covers a recessed portion 690. Thus, the pin 680 may rotate between the bottom of the chamber 645 and the flange 685. The chamber 645 is dimensioned to have the rear wall 655 juxtaposed with an edge 695 of the spaced apart walls 670 along the entire path of the light deflector 665, as the plug 405 is being advanced or withdrawn from the receptacle 450. Furthermore, the rear wall 655 has a curvature of the same radius as the edge 695. As shown, the spaced apart walls 670 of the light deflector 665 have a triangular cross-section; however, any other cross-section allowing the light deflector 665 to swing into and out of the light path can be easily implemented. Only one advantageous embodiment is illustrated in the figures, however it will be apparent to those skilled in the art that many different embodiments may be possible for implementing the light deflector 665. For instance, the light deflector may be rotatable, to rotate into the path of the light as shown, but it may also be slideable, or alternatively a sensor for sensing the presence of the plug 405 in the receptacle 450, may act to disconnect, obstruct, attenuate or turn off the source of light 310 upon removal of the plug 405 from the receptacle 450. Any of these or other methods may be utilized to prevent the light from escaping upon disconnection.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A video imaging system for viewing an area to be viewed, the system comprising:
    an endoscopic device, for transmitting illuminating light to and transmitting reflected light from, an area to be viewed;
    a camera, coupled to the endoscopic device, said camera generating image data based upon the received reflected light, said camera including:
        camera information relating to said camera; and
        a multiplexer;
    a camera control unit generating a command signal for operating said camera based on received camera information;
    a light source, coupled to said camera control unit, for generating illuminating light;
    a cable, coupling said camera to said camera control unit, said cable including:
        a pair of wires, for transmitting the image data and for transmitting camera information from said camera to said camera control unit; and
        a light guide, coupled to said light source, for transmitting illuminating light from said light source to said camera;
    said image data, the command signal and camera information multiplexed on said pair of wires.

2. The video imaging system according to claim 1 wherein at least the image data and the camera information are transmitted utilizing a digital serial protocol.

3. The video imaging system according to claim 2 wherein the digital serial protocol is Low-Voltage Differential Signaling.

4. The video imaging system according to claim 1 further comprising a jacket, enclosing said pair of wires and said light guide.

5. The video imaging system according to claim 1 wherein the control unit further comprises a light deflector mounted along a path between said light source and said light guide so as to sever the path of the light output when the cable is disconnected from the control unit.

6. The video imaging system according to claim 1 wherein said camera control unit further comprises a de-multiplexer for de-multiplexing the image data and camera information.

7. The video imaging system according to claim 1 further comprising a coupling attached to a distal end of said cable, for coupling said cable to said camera, said coupling including therein a connection for said pair of wires and said light guide.

8. The video imaging system according to claim 7 wherein said coupling engages with a longitudinal end of said camera and illuminating light is transmitted longitudinally through said camera to illuminate an area to be viewed.

9. A method for communicating between a camera and a camera control unit comprising the steps of:
    coupling a camera control unit to a camera via a cable, the cable including a pair of wires and a light guide;
    transmitting camera information from the camera to the camera control unit;
    generating a command signal based on the received camera information;
    transmitting a command signal from the camera control unit to the camera;
    generating illuminating light and transmitting the illuminating light to the camera via the light guide;
    transmitting the illuminating light from the camera to an area to be viewed via an endoscopic device coupled to the camera and receiving reflected light from the area to be viewed;
    generating image data based on the received reflected light;
    multiplexing the image data, the command signal and camera information to form a multiplexed signal; and
    transmitting the multiplexed signal via the pair of wires to the camera control unit.

10. The method according to claim 9 further comprising the step of de-multiplexing the multiplexed signal.

11. The method according to claim 9 wherein the camera control unit generates a command signal based on the received camera information.

12. The method according to claim 11 further comprising the step of multiplexing the command signal for transmission from the camera control unit to the camera via the pair of wires.

13. The method according to claim 9 wherein the cable is coupled to a longitudinal end of the camera.

14. The method according to claim 13 wherein the illuminating light is transmitted longitudinally through the camera to the area to be viewed.

* * * * *